United States Patent [19]

Bousset et al.

[11] Patent Number: 5,288,895
[45] Date of Patent: Feb. 22, 1994

[54] PROCESS FOR THE PREPARATION OF A BIPHENYL DERIVATIVE

[75] Inventors: Michel Bouisset; Alain Boudin, both of Sisteron, France

[73] Assignee: Elf Sanofi, Paris, France

[21] Appl. No.: 45,519

[22] Filed: Apr. 6, 1993

[30] Foreign Application Priority Data

Apr. 13, 1992 [FR] France ................................ 92 04512

[51] Int. Cl.$^5$ ........................................... C07C 253/30
[52] U.S. Cl. ..................................... 558/378; 558/411
[58] Field of Search ................................. 558/378, 411

[56] References Cited

U.S. PATENT DOCUMENTS 4,942,221  7/1990  Moinet et al. ............. 558/378 X R

FOREIGN PATENT DOCUMENTS 0341514  11/1989  European Pat. Off. .
0470794  2/1992  European Pat. Off. .

OTHER PUBLICATIONS

Chemical Abstracts, vol. 75, (1971), Columbus, Ohio, U.S., Abstract No. 48572p Nakaya et al.
March, Advanced Organic Chemistry, 3rd Ed., (1985), pp. 828–829.
Rappoport, The Chemistry of the Cyano Group, (1970), pp. 314 and 331.

*Primary Examiner*—Joseph Paul Brust
*Attorney, Agent, or Firm*—Wegner, Cantor, Mueller & Player

[57] ABSTRACT

The subject of the invention is a process for the preparation of 4-methyl-2'-cyanobiphenyl of formula:

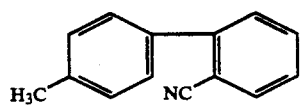

I wherein a benzonitrile halide of general formula:

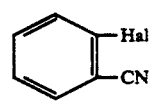

II in which Hal represents a halogen atom, is reacted, in the presence of a manganese salt, with an organometallic derivative of general formula:

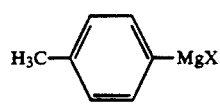

III in which X represents a halogen atom, and the complex obtained is then hydrolysed, which provides the desired compound.

8 Claims, No Drawings

PROCESS FOR THE PREPARATION OF A BIPHENYL DERIVATIVE

The present invention generally relates to a new process for the preparation of a biphenyl derivative.

More precisely, the subject of the invention is a new process for the preparation of 4-methyl-2'-cyanobiphenyl of formula:

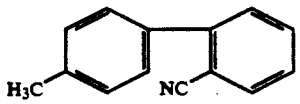

I

4-Methyl-2,-cyanobiphenyl can be widely used as an intermediate, especially for the final synthesis of biphenylmethylimidazoline derivatives described in patent applications EP-A-0,253,310 and 0,454,511.

These imidazoline derivatives have proved to be useful due to their pharmacological properties, especially their angiotensin II antagonist properties.

These properties make the compounds in question particularly advantageous in the treatment of syndromes of the cardiovascular system such as hypertension or heart failure and in the treatment of diseases of the central nervous system and in the treatment of glaucoma and of diabetic retinopathy.

Various methods have been reported in the chemical literature making possible the preparation of 4-methyl-2'-cyanobiphenyl.

In this respect, there may be mentioned the process described in J. Med. Chem., 34, pp. 2525-2547 (1991), according to which process:

a) 2-methoxybenzoic acid is reacted with thionyl chloride;
b) the acyl chloride formed is treated with 2-amino-2-methyl-1-propanol, which provides an amide in the crude form;
c) this amide is subjected to the action of thionyl chloride, and 4,4-dimethyl-2-(2-methoxyphenyl-)oxazoline (yield 88% from the acyl chloride) is thus formed;
d) this oxazoline derivative is reacted with p-tolylmagnesium bromide and the complex formed is hydrolysed, which gives 4,4-dimethyl-2-(4'-methylbiphenyl-2-yl)oxazoline (yield 91%);
e) the oxazoline derivative formed is then treated with phosphorus oxychloride, which finally provides 4-methyl-2'-cyanobiphenyl (yield 96%).

Consequently, the compound of formula I can be synthesised with an overall yield of 77% according to this method. Nevertheless, this process has especially the disadvantage of requiring the use of 5 stages, starting from commercially available products, due to the prior information of the dimethyloxazolinyl group and its subsequent conversion to the cyano group.

Additionally, the formation of the 2-methoxybenzoyl chloride requires a prolonged treatment (18 hours) using thionyl chloride.

Moreover, patent application EP-A-0,470,794 has reported a process making possible the preparation of cyanobiphenyl derivatives, especially 4-methyl-cyanobiphenyl derivatives, according to which process a metal or organometallic 4-methylphenyl derivative is reacted with a bromobenzonitrile in the presence of a metal catalyst chosen from a catalyst based on Pd(0), Pd(II), Ni(0) and Ni(II).

According to Example 2 of this Patent Application, 4-methyl-2'-cyanobiphenyl is obtained by reaction of p-tolyltributyltin and 2-bromobenzonitrile in the presence of tetrakis(triphenylphosphine)palladium(0), with a yield of 63%. However, this process has especially the disadvantage of requiring a very prolonged reaction time (36 hours) and the additional formation of p-tolyltributyltin from p-tolylmagnesium bromide.

The search for an industrial process for the preparation of 4-methyl-2'-cyanobiphenyl using a minimum of stages, easily accessible and inexpensive intermediates and providing a satisfactory yield of final product remains of indisputable interest.

It has now been found, surprisingly, that it is possible to prepare 4-methyl-2'-cyanobiphenyl also starting from a p-tolylmagnesium halide, but according to an industrial process, in a single stage, providing significant yields of the desired compound.

Thus, the process of the invention for the preparation of the compound of formula I consists in reacting, in the presence of a manganous salt, a benzonitrile halide of general formula:

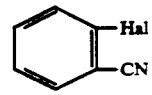

II in which Hal represents a halogen atom, preferably chlorine, with an organometallic derivative, namely a magnesium derivative of general formula:

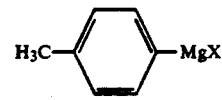

III in which X represents a halogen atom, preferentially bromine, and in then hydrolysing the complex obtained, which provides the desired compound.

The reaction can be carried out according to the standard methods of employing organometallic derivatives, namely in an anhydrous ether such as tetrahydrofuran, dibutyl ether or dioxane, and at a temperature of, for example, between −10° C. and room temperature.

Likewise, the hydrolysis of the complex can be carried out according to known procedures, for example by means of an acid such as hydrochloric acid, in aqueous solution. Generally, the organometallic derivative of formula III is used at a concentration of 1.5 to 2.5 mol per mole of benzonitrile derivative of formula II, preferably 2 mol of compound of formula III.

As for the manganous salt, it can be especially a manganous halide, for example the chloride, bromide or iodide.

Preferentially, manganous chloride is used, given its commercial availability and its fairly low cost. This manganese salt can be used at a concentration of 0.05 to 1 mol per mole of benzonitrile halide of formula II.

Indeed, it has been noticed that low concentrations, indeed virtually catalytic concentrations, of manganous salt, such as 5 to 10 mole %, can be legitimately used for the implementation of the process of the invention.

The use of very small amounts of manganous salt has an advantage, especially during the purification of the compound of formula I. Indeed, as the residual manganese salts have little solubility in the reaction mixture, their presence in very small amounts, in this medium, makes their separation easier by settling.

According to a preferred implementation of the process of the invention, the organometallic derivative of formula III is added to a mixture of compound of formula II and of manganous salt in an ether.

However, there can also be envisaged the addition of the benzonitrile derivative of formula II to a solution of manganous salt and of organometallic derivative of formula III in an ether.

Preliminary tests carried out in the context of the present invention showed that p-tolylmagnesium bromide, in the presence of 2-chlorobenzonitrile, but in the absence of manganese salt, proves to be incapable of giving 4-methyl-2'-cyanobiphenyl.

For example, a test was carried out by adding, at a temperature of 10° C.±2° C. and for 1 h 20 minutes, 70 ml of a solution of p-tolylmagnesium bromide (0.085 mol; 1.22 equivalent) in tetrahydrofuran to a solution of 9.6 g (0.07 mol) of 2-chlorobenzonitrile in 20 ml of tetrahydrofuran and by maintaining the mixture at this temperature for 3 h 10 minutes.

After hydrolysis by means of 3.7% hydrochloric acid and extraction with ethyl acetate, an analysis by high pressure liquid chromatography (HPLC) showed the predominance of 2-chlorobenzonitrile in the mixture, as well as the addition product of the magnesium derivative to the nitrile, namely(2-chloro-1-phenyl(4-tolyl) ketone.

However, no trace of 4-methyl-2,-cyanobiphenyl was observed.

Moreover, comparative tests were carried out according to the operating conditions indicated in patent application EP-A-0,470,794, and especially according to the operating conditions of Example 2 of this Patent Application.

To this end, the process below was used:

In a three-necked, round-bottomed flask, a solution of 1 equivalent of 2-bromobenzonitrile and Y equivalent of catalyst in tetrahydrofuran was prepared under an inert atmosphere.

X equivalent of p-tolylmagnesium bromide, hereafter called A-MgBr, or p-tolyltributyltin, hereafter called A-SnBu$_3$, were then run in at the temperature T. At the end of the addition, the reaction mixture was maintained at the same temperature for a time t. Hydrolysis was then carried out with a 5% hydrochloric acid solution and finally with water. The aqueous phase was extracted with toluene, the organic phases were combined and were washed with water, with a 5% aqueous potassium carbonate solution and finally with water.

The 4-methyl-2'-cyanobiphenyl yield was then determined, by assaying of this compound in the residue from the evaporation of the organic phase.

The following results were obtained by using PdCl$_2$, NiCl$_2$ or Pd(PPh$_3$)$_4$ as catalyst, Ph representing the phenyl radical:

| X (equivalent) | Y (equivalent) | T(°C.)/t (h) | Yield (%) |
|---|---|---|---|
| 4.2 A-MgBr | 0.3 PdCl$_2$ | 0/4 | 22 |
| 3.0 A-MgBr | 0.3 NiCl$_2$ | 0/4 | 27 |
| 1.0 A-SnBu$_3$ | 0.003 PdCl$_2$ | 65/14 | 1 |
| 1.0 A-SnBu$_3$ | 0.3 PdCl$_2$ | 65/20 | 6 |
| 1.0 A-SnBu$_3$ | 0.003 NiCl$_2$ | 65/14 | 0 |
| 1.0 A-SnBu$_3$ | 0.3 NiCl$_2$ | 65/20 | 0 |
| 4.0 A-MgBr | 0.003 Pd(PPH$_3$)$_4$ | 0/5 | 1 |
| 2.2 A-MgBr | 0.003 Pd(PPH$_3$)$_4$ | 65/6 | 1 |

Additional tests carried out according to the same conditions of the sate of the art, but using a catalyst according to the invention, namely MnCl$_2$, provided the following results:

| X (equivalent) | Y (equivalent) | T(°C.)/t (h) | Yield (%) |
|---|---|---|---|
| 1.0 A-SnBu$_3$ | 0.3 MnCl$_2$ | 65/14 | 1 |
| 1.0 A-SnBu$_3$ | 0.003 MnCl$_2$ | 65/20 | 0 |

Likewise, other comparative tests have been carried out by using operating conditions according to the invention, starting from one equivalent of 2-chlorobenzonitrile and using, as organometallic derivative, either p-tolylmagnesium bromide, according to the invention, or p-tolyllithium, hereafter called A-Li, according to the state of the art.

The following results were recorded:

| Organometallic derivative | Manganous salt (equivalent) | T(°C.)/t (h) | Yield (%) |
|---|---|---|---|
| 2.0 A-Li | 0.3 MnCl$_2$ | 0/4 | 0 |
| 1.73 A-MgBr | 0.2 MnCl$_2$ | 10/0.25 | 70 |
| 1.74 A-MgBr | 0.1 MnCl$_2$ | 10/0.25 | 70 |

These results show the marked superiority of the process of the invention over the prior processes.

As mentioned above, the compound of formula I can give access to biphenylmethylimidazoline derivatives described especially in patent applications EP-A-0,253,310 and 0,454,511.

Depending on the situation, the reaction scheme below will be used in the order shown, or in reverse order, namely:

a) the substitution of the methyl group of the compound of formula I according to known methods, for example by a coupling reaction, in basic medium, by means of a suitable compound, and after halogenation of this methyl group, b) the conversion of the cyano group of the compound of formula I according to standard processes such as, for example, by means of tributyltin azide or sodium azide to form the tetrazolyl group.

The following non-limiting examples illustrate the process of the invention.

EXAMPLE 1

Preparation of 4-methyl-2'-cyanobiphenyl 9.6 g (0.07 mol) of 2-chlorobenzonitrile, 0.44 g or 5 mole % of anhydrous manganous chloride and 20 ml of dry tetrahydrofuran are placed in a three-necked, round-bottomed flask. 110 ml of a solution of p-tolylmagnesium bromide (0.135 mol; 1.93 equivalent) in tetrahydrofuran are then run in dropwise, while maintaining the temperature at 10° C. ±2° C. The addition requires approximately 1.5 h. The mixture is then maintained for 15 minutes at this temperature and is then hydrolysed at the same temperature with 100 ml of 3.7% hydrochloric acid. The mixture is allowed to settle and the aqueous phase is extracted with 100 ml of ethyl acetate. After concentration of the organic phases, 19.4 g of a brown viscous liquid are obtained, which liquid assays, by HPLC, 41% of desired product, which corresponds to a chemical yield of 60%.

In this way, 4-methyl-2'-cyanobiphenyl is obtained in the form of a beige solid after recrystallisations from ethanol. M.p. 47°–49° C.

EXAMPLE 2

Preparation of 4-methyl-2'-cyanobiphenyl

The same process is used as that of Example 1, starting from 0.88 g or 10 mole % of manganous chloride and 100 ml of p-tolylmagnesium bromide (0.122 mol; 1.74 equivalent) in tetrahydrofuran. After concentration of the organic phases, 18.3 g of a brown viscous liquid are obtained, which liquid assays, by HPLC, 51% of desired product, which corresponds to a chemical yield of 70%.

After ethanol recrystallisations, 4-methyl-2'-cyanobiphenyl can be isolated in the form of a beige solid.

EXAMPLE 3

Preparation of 4-methyl-2'-cyanobiphenyl

The same process is used as that of Example 1, starting from 1.76 g or 20 mole % of manganous chloride and 90 ml of p-tolylmagnesium bromide (0.121 mol; 1.73 equivalent) in tetrahydrofuran. After concentration of the organic phases, 16.3 g of a brown viscous liquid are obtained, which liquid assays, by HPLC, 50% of desired product, which corresponds to a chemical yield of 70%.

After ethanol recrystallisations, 4-methyl-2'-cyanobiphenyl can be isolated in the form of a beige solid.

EXAMPLE 4

Preparation of 4-methyl-2'-cyanobiphenyl

The same process is used as that of Example 1, starting from 8.8 g or 100 mole % of manganous chloride and 110 ml of p-tolylmagnesium bromide (0.123 mol; 1.76 equivalent) in tetrahydrofuran. After concentration of the organic phases, 17.4 g of a brown viscous liquid are obtained, which liquid assays, by HPLC, 58.5% of desired product, which corresponds to a chemical yield of 75%.

After ethanol recrystallisations, 4-methyl-2'-cyanobiphenyl can be isolated in the form of a beige solid.

We claim:

1. A process for the preparation of 4-methyl-2'-cyano biphenyl of formula:

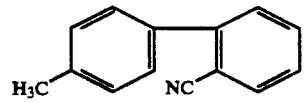

wherein a benzonitrile halide of general formula:

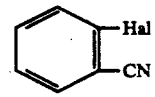

in which Hal represents halogen, is reacted, in the presence of a manganous salt, with an organometallic compound of general formula:

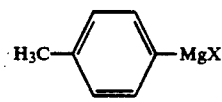

in which X represents halogen and the complex obtained is then hydrolysed, which provides the desired compound.

2. A process according to claim 1, wherein Hal represents chlorine.

3. A process according to claim 1, wherein X represents bromine.

4. A process according to claim 1, wherein the manganous salt is manganous chloride.

5. A process according to claim 1, wherein from 1.5 to 2.5 mol of organometallic compound of formula III are used per mole of benzonitrile halide of formula II.

6. A process according to claim 1, wherein from 0.05 to 1 mol of manganous salt is used per mole of benzonitrile halide of formula II.

7. A process according to claim 1, wherein the complex is hydrolysed by means of an acid.

8. A process according to claim 1, wherein the reaction is carried out at a temperature between −10° C. and room temperature.

* * * * *